United States Patent [19]
Groner

[11] Patent Number: 5,851,835
[45] Date of Patent: Dec. 22, 1998

[54] MULTIPARAMETER HEMATOLOGY APPARATUS AND METHOD

[75] Inventor: Warren Groner, Great Neck, N.Y.

[73] Assignee: Center For Laboratory Technology, Inc., Great Neck, N.Y.

[21] Appl. No.: 764,322

[22] Filed: Dec. 12, 1996

Related U.S. Application Data

[60] Provisional application No. 60/008,818 Dec. 18, 1995.
[51] Int. Cl.$^6$ ..................................................... G01N 33/48
[52] U.S. Cl. .............................. 436/63; 436/66; 436/70; 436/164; 422/73; 422/82.05; 382/133; 382/134; 356/39; 356/40; 356/317; 356/318; 356/336; 356/337
[58] Field of Search .................................. 436/63, 66, 69, 436/70, 164, 165; 422/73, 82.05, 82.09; 435/2; 382/133, 134; 356/39, 40, 300, 311, 317, 318, 336, 337

[56] References Cited

U.S. PATENT DOCUMENTS

| | | | |
|---|---|---|---|
| 4,338,024 | 7/1982 | Bolz et al. | 356/23 |
| 4,341,471 | 7/1982 | Hogg et al. | 356/343 |
| 4,596,035 | 6/1986 | Gershman et al. | 382/134 |
| 4,735,504 | 4/1988 | Tycko | 356/336 |
| 4,882,284 | 11/1989 | Kirchanski et al. | 436/63 |
| 5,072,382 | 12/1991 | Kamentsky | 382/133 |
| 5,241,369 | 8/1993 | McNeil et al. | 356/445 |
| 5,378,633 | 1/1995 | von Behrens et al. | 436/63 |
| 5,510,267 | 4/1996 | Marshall | 436/63 |

FOREIGN PATENT DOCUMENTS

| | | |
|---|---|---|
| 0507746 | 10/1992 | European Pat. Off. |
| 0575712 | 12/1993 | European Pat. Off. |
| 0582431 | 2/1994 | European Pat. Off. |
| 0641542 | 3/1995 | European Pat. Off. |
| 2219083 | 11/1989 | United Kingdom. |

OTHER PUBLICATIONS

Annual Review of Biophysics and Bioengineering, vol. II, 1982.

Primary Examiner—Maureen M. Wallenhorst
Attorney, Agent, or Firm—Dilworth & Barrese

[57] ABSTRACT

A multi-parameter hematology analyzer and method are provided for in vitro determination of blood parameters. The analyzer apparatus includes a laser for transmitting light through a specimen container containing a minimally diluted blood sample. The light scattered by the constituents of the blood sample are scattered into a pattern which is recorded on a camera image. This image is then processed by image processing software and is used to establish specific blood parameters.

18 Claims, 1 Drawing Sheet

BLOCK DIAGRAM OF RBC MEASUREMENT

MULTIPARAMETER HEMATOLOGY APPARATUS AND METHOD

CROSS REFERENCE TO RELATED APPLICATION

This application claims priority to provisional application Ser. No. 60/008,818, filed Dec. 18, 1995.

BACKGROUND

1. Field of the Invention

This invention relates to diagnostic hematology apparatus and, more particularly, to apparatus and methods for obtaining diagnostic information such as cell concentration and sizing using ensemble light scattering.

2. Description of the Related Art

The current methods of cell counting and sizing are both accurate and precise. However, since they must detect individual blood in a sensing zone which is generally quite large when compared to a blood cell they require high dilutions prior to measurement which must be calibrated and maintained by the use of labile materials. This need for high dilution also increases the complexity of the apparatus and renders the use of these devices impractical in more remote locations such as: primitive (third world countries); battle field/disaster site; Doctor's office; and Emergency room. For these applications it is desirable to consider alternative means, requiring little or no blood dilution prior to measurement, that are simple to implement and do not require labile materials for calibration or quality control.

One means of estimating the concentration of blood cells without dilution is by packing the cells with centrifugal force and measuring the length of the packed column relative to the total length. Since the cells of different class (RBC WBC and PLT) have different density, they may be layered by this procedure allowing a measurement of concentration by class. This general method has been developed for use in remote areas such as those listed above. Becton Dickenson has marketed a device based on a these principles called the QBC. However, this device has two serious deficiencies, i.e., accurate operation requires operator skill in visually estimating the boundaries between cell classes; and the device is unable to determine the mean red blood cell volume which is an important measurement in the diagnosis of anemia.

Another means of estimating the concentration and/or size of cells at low dilution is to observe the diffraction and/or scattering of light by ensembles of blood cells. This method has been used to estimate cell concentration by measuring the turbidity of cell suspension, to estimate cell size by measuring the diameter of the rings formed when light is diffracted by RBC dried on a glass slide or in liquid suspension, and to discriminate between cell population based on the angular distribution of the scattered light and to measure the average deformation of RBC when under hydrodynamic stress.

However, these techniques have not been combined and are not commonly used today having been replaced by the current methods of counting and sizing individual cells while passing through a small aperture.

SUMMARY

Ensemble light scattering is used as the fundamental technology for a multi-parameter hematology analyzer. It is expected by considering the application of this technology, benefit may be gained by synergy with advances in related technology which make the application more practical today. Such advances include the common availability (at low cost) of coherent light sources (lasers) and the growing availability (also at low cost) of the software and hardware required to digitize and analyze electronic images. Such devices as CCD cameras, personal computers and video phone interphases developed for the consumer market may be applicable directly to this device.

There is benefit in that a high dilution is not required, therefore simplifying the device.

A second benefit is the elimination of the requirement to meter the diluted blood through a small aperture, therefore further simplifying the device.

A third benefit is derived in that the measurement time is reduced. Instruments which count cells one at a time must allow time for the accumulation of cell counts, whereas the combined effect of a multiplicity of cells are measured instantaneously when ensemble scattering is employed.

A fourth benefit may result from applying the same root technology to other aspects of diagnostic hematology. For instance, ensemble scattering has been used to measure RBC deformability and aggregation of platelets. Ensemble scattering may also be useful in measuring the cell/cell interaction which are the dominant factor in the sedimentation of erythrocytes. Thus, these additional measurements may be more easily combined into a single device which in addition to the traditional measurement of cell count and cell size also measures the ESR.

BRIEF DESCRIPTION OF THE DRAWINGS

The accompanying drawing, referred to herein and constituting a part hereof illustrates a preferred embodiment of the apparatus of the present invention, and, together with the description serve to explain the principles of the invention.

DETAILED DESCRIPTION OF PREFERRED EMBODIMENTS

Figure 1:
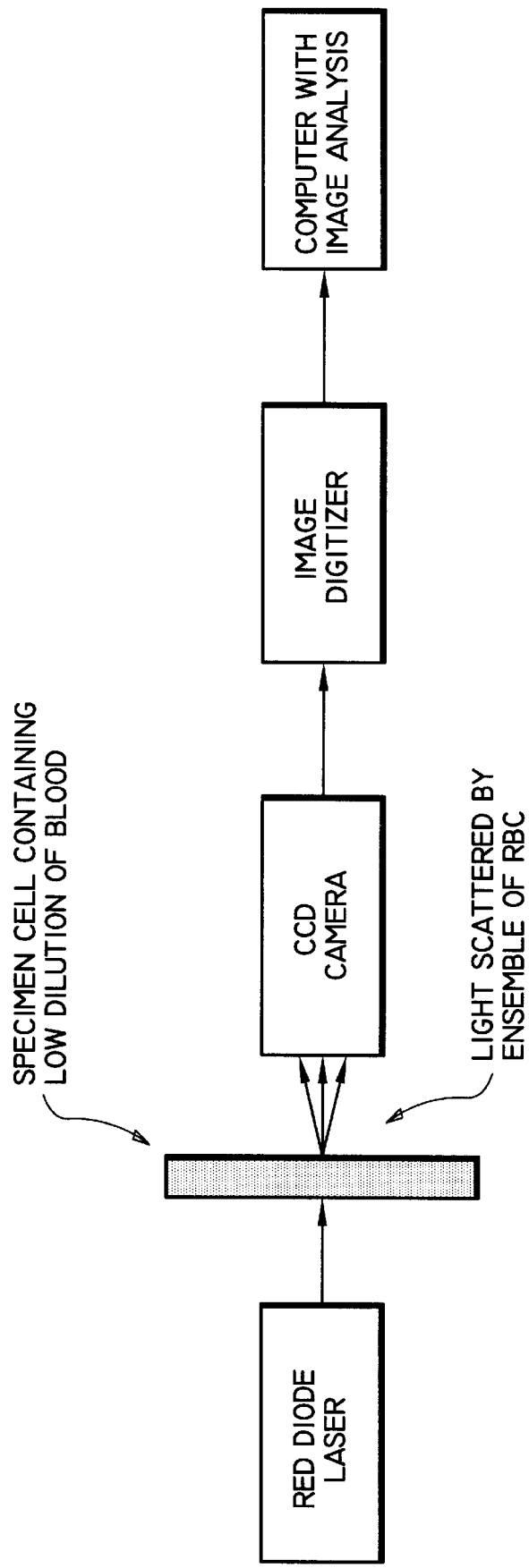
FIG. 1 is a block diagram of an apparatus in accordance with the present invention.

The scattering of coherent light by a small, single particle is equivalent to transforming the morphology of the particle into the angular distribution of scattered light. Mathematically this transform is known as the Fourier transform. This is a well known effect and for some classes of particles such as spheres, the transform is known exactly. When a collimated beam of coherent light encounters a system of biological cells or structures, part of the light may be absorbed, part is scattered, and the rest is transmitted. Transmitted and scattered light are measured to obtain information about the cells.

The scattering of coherent light by an ensemble of particles which all are within the coherence length of light source is obtained by the superposition of the light scattered by individual particles. Thus, if the particles are uniform and dispersed randomly, the net scattering distribution is N times the scattering intensity of a single particle where N is the number of particles. This is also a well known effect which has been used to both size and estimate the concentration of particles. These measurements may be made directly on the angular distribution of the scattered light or after performing a Fourier transform of the angular distribution.

If the particles are not randomly dispersed, then the scattering from individual particles "interfere", creating a distribution of scattering intensity reflecting the organization of the individual particles. As a result, the tendency of particles to aggregate may be determined by measuring the fluctuations in intensity of the scattered light. If the particles are random, the "interferences" between the scattering from individual particles are also random leading to a uniform and constant fluctuation at any angle. However, as particles begin to aggregate, the interference grows, leading to increased fluctuation.

Hematology parameters discernable using ensemble light scattering include: white blood cell count (WBC); red blood cell count (RBC); platelet count (PLT); mean cell volume (MCV); mean cell hemoglobin (MCH); mean cell hemoglobin concentration (MCHC); percentage of granulocytes (GRAN); percentage of agranulocytes (AGRAN); percentage of polymorphonuclear cells (POLYS); percentage of mononuclear cells (MONO); and erythrocyte sedimentation rate (ESR).

Table 1 set out below catalogs the normal ranges for these parameters as well as the respective diagnostic utilities therefor.

TABLE 1

| Parameters | Symbol | Normal Range | Utility |
|---|---|---|---|
| White Blood Count | WBC | 5000–12000 Cells/MM$^3$ | If Elevated - Infection/Inflammation |
| Red Blood Cell Count | RBC | 4,000,000 to 6,000,000 Cells/MM$^3$ | If Depressed - Anemia |
| Platelet Count | PLT | 175,000 to 3,000,000 Cells/MM$^3$ | If Depressed - Possible Clotting Problem |
| Mean Cell Volume | MCV | 80–95 × 10$^{-12}$ Liter | If Elevated - Vitamin Deficiency If Depressed - Iron Deficiency |
| Mean Cell Hemoglobin | MCH | 25–35 Picogram | Same As Mean Volume |
| Mean Cell Hemoglobin Concentration | MCHC | 32–16 Picogram Per Femtolitre | If Depressed - Severe Anemia |
| Granulocytes | GRAN | 40–75% WBC | If Elevated - Infection/Inflammation |
| Agranulocytes | AGRAN | 25–60% WBC | If Elevated - Virus |
| Polymorphonuclear Cells | POLYS | 40–75% WBC | Same As Granulocytes |
| Mononuclear Cells | MONO | 25–60% WBC | Same As Agranulocytes |
| Erythrocyte | ESR | 10 MM/Hous | If Elevated - Infection/Inflammation |

FIG. 1 illustrates a specific example of the concept of using ensemble scattering to obtain the measurement of RBC. The light from a laser is scattered by a thin transparent specimen container containing a low (10–100) dilution of whole blood.

Appropriate lasers are well known in the art and include, inter alia, He, Ne, Gas, GAAS diode lasers. The specifications for the preferred laser are that it emits in the red spectrum and is of a beam diameter which is less than the specimen container width. The coherence should be greater than cell length and the power level is preferably about 1 milliwatt.

The specimen container should have a high degree of optical clarity and a path length through the container of at least about 0.1 mm. The optical path length should be such that there is a reasonable probability that the light will be scattered by one blood cell while a much lower probability that the light will be multiply scattered by several blood cells. For this reason the optical path length should be roughly equal to the average distance between blood cells. For example:

10×Dilution→Mean Distance=0.06 mm

100×Dilution→Mean Distance=0.13 mm

Such a specimen container is the BMS-10150, available from Federich Dimmock Co. The BMS-10150 has dimensions of 0.1 mm×1.0 mm×50 mm.

Examples of preparation methods for dilution of whole blood are set forth in Table 2 below. In the measurement column, the specific parameters measurable from respective solutions are set forth.

TABLE 2

| Dilution | Dilution/Method | Specific Example | Measurement |
|---|---|---|---|
| 1/1–1/10 | Isotonic Buffered Saline with Anti-Coagulant | Trisodium Citrate Di-Hydrate (Na$_3$C$_6$H$_5$O$_7$:H$_2$O) At A Concentration Of 100–136 MMOL | RBC Aggregation |
| See Note | Isotonic Reagent Containing An Active Ingredient To Sphere RBC At Constant Volume | 1/10 Dilution of Whole Blood In An Isotonic Buffer Containing Sodium Dodecyl Sulfate At 0.035 MMOL Specifically: RBCDIL, Prod. # TO1-1570-56 Available From Bayer Diagnostics, Tarrytown, NY | MCV, RBC MCH, MCHC PLT/RBC |
| See Note | Hemolytic Reagent Capable Of Destroying RBC While Preserving WBC | 1/10 Dilution Of Whole Blood In A Reagent Containing A Surfactant. Specifically: Cell-DYN 3000 Sheath Part # 9900311 Available From Abbott Diagnostics, Abbott Park, IL | WBC ORAN AGRAN |
| See Note | Hemolytic Reagent Capable Of Destroying RBC AND Lysing WBC | 1/10 Dilution of Whole Blood In A Reagent Containing Phthalic Acid at 21.5 MMOL Specifically: BASO DIL, Prod. # TO1-1645-56 Available From Bayer Diagnostics, Tarrytown, NY | WBC Platelet Poly Mono |

NOTE: Dilution to be nominally sufficient so that the mean distance between cells is approximately equal to the path length of the measurement cell.

The pattern from the scattering is imaged on a CCD camera. The CCD camera is preferably monochromatic with at least 350,000 pixel capacity. One such camera is the model KRMI, available from Hitachi Denshi, Ltd.

The resultant image is then captured and digitized through a digitizing means. The digitizing means is also preferably monochromatic with at least 8 bit high accuracy analog to digital capability. A digitizing means meeting these requirements is the model DT 3155 Frame Grabber, available from Data Translation. The digitized image is then analyzed with a small computer containing a resident image processing software program.

The computer can be any of a wide variety of known microprocessors including the 486 and Pentium microprocessors capable of running the image analysis software. One software package suitable for the present image analysis is Global Lab Image Version 3.1, available from Data Translation.

As a general rule, particles larger than the wavelength of light such as, e.g. RBC; scatter mostly at forward angles (0°–10°, preferably 0°–5°). Thus, the portion of the total light scattered by the cell is proportional to the scattering measured at the small forward angles.

For dilution of whole blood, the distribution of scattered light is dominated by the RBC which are the principal cell type. The diameter of the first ring of the circularly symmetry scattering pattern can be used to estimate the average diameter of the RBC. Equation 1 gives a formula which has been used previously to obtain the average cell diameter in terms of the radius (r) of the first ring of light scattered at wavelength (2) when focussed with a camera lens of focal length (f).

The concentration of RBC can be determined from the turbidity of the solution. Equation 2 gives a formula relating the cell concentration (c) in terms of the $$d = 1.7\lambda \frac{\sqrt{f^2 + r^2}}{r} \quad (1)$$

measurement of relative intensity (I), the average cell diameter (d), the path length (b) and the wavelength of light (lambda).

$$\text{Log} I/I_0 = \frac{bcd^3}{d^4 + a\lambda^4} \quad (2)$$

Obviously, the result from equation 1 can be used in equation 2, eliminating the ambiguity generally associated with estimates of cell concentration due to the size of the particles.

The time variation in intensity of the scattered light may be used to determine the rate of aggregation and sedimentation. Two effects govern this determination; first, there is a steady increase in light transmission (reduction in turbidity) as a greater proportion of the RBC that are hidden by their neighbors, and second, there is an increase in the fluctuation of intensity due to coherent interference between the scattering from individual RBC. These contributions can be used to estimate the erythrocyte sedimentation rate (ESR).

Thus, with a simple device used with a single low dilution of whole blood, one is able to determine the three most important clinical results characteristics of the RBC population:

1) Cell concentration (detection of anemia);
2) Cell size (classification of anemia); and
3) Sedimentation rate (detection of infection/inflammation).

As a second specific example consider the measurements on WBC. The sample apparatus as illustrated previously may be used. However, in this case the fluid used to obtain the low dilution of whole blood must contain an agent which hemolyzes the RBC and destroys their membrane. Phthalic acid at 21.5 mmol may be used. Under these conditions the dominant scattering cell population is the WBC.

It is well known that two populations of WBC are typical. The first and most dominant are the granulocytes (neutrophils, basophils, and eosinophils) while the second (ymphocytes and monocytes) contain no or few granules. The light scattered from a solution of intact WBC similarly demonstrates two components with the scattering at low angle dominated by the non-granular cells and the scattering at high angles dominated by the granular cells. Therefore, by measuring the ratio of intensity at different angles, a result related to the ratio of the two cell populations can be obtained.

Thus, as with the RBC measurements described previously using a simple apparatus and one low dilution of whole blood, two of the most clinically significant results regarding the WBC may be obtained. That is:

1) Cell concentration; and
2) Ratio of granulocytes to non-granulocytes.

With respect to the red cell indices of MCV and MCHC, ratios of ensemble scattering at two angles can be used. This technique, as applied to individual sphered particles, is set forth in U.S. Pat. No. 4,735,504 to Daniel H. Tycko, the disclosure of which is incorporated herein by reference. Using this technique, monochromatic light is passed through the cell population to produce one forward light scattering pattern. By measuring this forward light scattering at two selected angular intervals, values at each angle are discerned. The first angular interval is preferably selected to span the angular region within which the first maxima of the light scattering patterns of the cell populations having volumes in the physiological range are expected to fall.

The second angular interval is selected which begins above the upper limit of the first angular interval and below the second maximum of the scattering pattern of the cell population. By comparing the signals generated at the first and second intervals, as a pair with signals generated by cell populations of known volume and index of refraction, MCV and MCHC can be determined.

For determinations of fractional cell concentrations of, e.g. PLT/RBC, GRAN/WBC, GRAN/AGRAN, MONO/POLY or POLY/WBC, a physical mask is employed to isolate the region of scattering that differentiates the population of interest, i.e. for platelets which are smaller than RBC one might isolate the high angles of scatter in comparison with the value for the total scattering. For example, a more specific estimate of the PLT/RBC fraction can be made by using a mask which is the inverse of the RBC scattering pattern. Thus, the light that gets through the mask corresponds to some other cell type such as PLT. Comparing intensity with and without such a mask estimates the concentration of PLT.

Similarly, a virtual (hypothetical with values) or algorithmic mask may be entered into the image analysis stage to achieve the same effect as interposing the physical mask before the camera. In this case the digital data corresponding to the ensemble scattering of the cell population will be filtered to enhance the contribution of a particular constituent, e.g. RBC, WBC, AGRAN or POLY. The values generated after the virtual mask are then analyzed to generate the desired fractional cell concentrations.

For cell aggregation measurements, e.g. ESR, values for turbidity or light scattering intensity are determined as a function of time. Alternatively, the fluctuations in intensity can be measured as a function of time.

It will be understood that various modifications may be made to the embodiments shown herein. The above description should not be construed as limiting, but merely as exemplifications of preferred embodiments. Those skilled in the art will envision other modifications within the scope and spirit of the claims appended hereto.

What is claimed is:

1. A multiparameter hematology apparatus comprising, in combination:

a source of light energy configured to emit laser light in a red spectrum;

a reservoir for containing a blood specimen diluted to less than 1/100 the reservoir having a transparent portion in line with the laser light emitted from the source of light energy and providing access to an ensemble light scattering pattern from the blood specimen;

a camera disposed in line with the transparent portion for receiving the ensemble light scattering pattern of the laser light from an ensemble of blood cells contained in the specimen and providing images thereof;

a digitizing means for digitizing the images, in operative communication with the camera for receiving frames of images of the ensemble light scattering pattern and converting at least a portion thereof into digital images; and a processor connected to the digitizing means for performing image analysis on the digital images of the ensemble light scattering pattern to establish blood parameters therefrom including intrinsic parameters such as cell size, extrinsic parameters such as cell counts as well as aggregation and sedimentation of blood cells.

2. The apparatus of claim 1, wherein the source of light is selected from the group consisting of a He Ne laser and a diode laser.

3. The apparatus of claim 1, wherein the reservoir for containing a blood specimen is a transparent specimen container configured to define a path width therethrough of from about 0.1 mm to about 0.5 mm.

4. The apparatus of claim 1, wherein the camera comprises a monochrome CCD camera.

5. The apparatus of claim 4, wherein the monochrome CCD camera has greater than about 350,000 pixels.

6. A method for making measurements of a blood cell population comprising the steps of:

providing a multiparameter hematology apparatus having a source of light energy configured to emit coherent light in a red spectrum, a transparent reservoir for containing a blood specimen diluted to less than 1/100,a camera for receiving an ensemble light scattering pattern from an ensemble of blood cells contained in the specimen contained in the reservoir and providing images thereof a digitizing means for digitizing images in operative communication with the camera for receiving and converting the images into digital images and a processor operatively connected to the digitizing the means for performing image analysis on the digital images;

providing a blood specimen diluted to less than 1/100 in the transparent reservoir of the multiparameter hematology apparatus;

irradiating the specimen with light from the source of light energy in the red spectrum;

picking up the ensemble light scattering pattern from the irradiated ensemble of blood cells contained in the specimen with the camera; and converting the images of the ensemble light scattering pattern into digital images with the digitizing means ,and processing the digitized images of the ensemble light scattering pattern with the process to establish blood parameters for the blood specimen including intrinsic parameters such as cell size, extrinsic parameters such as cell counts as well as aggregation and sedimentation of blood cells.

7. The method as in claim 6, wherein the blood specimen is diluted with isotonic buffered saline including an anticoagulant and the established blood parameters are selected from the group consisting of red blood cell count and aggregation of blood cell.

8. The method as in claim 6, wherein the blood specimen is diluted with an isotonic reagent containing an active ingredient to sphere RBC (red blood cells) at constant volume and the established blood parameters are selected from the group consisting of MCV (mean cell volume), RBC, MCH (mean cell hemoglobin), MCHC (mean cell hemoglobin concentration), and PLT (platelets)/RBC.

9. The method as in claim 6, wherein the blood specimen is diluted with a hemolytic reagent configured to destroy RBC (red blood cells) while preserving WBC (white blood cells) and the established blood parameters are selected from the group consisting of WBC, GRAN (percentage of granulocytes), and AGRAN (percentage of agranulocytes).

10. The method as in claim 6, wherein the blood specimen is diluted with a hemolytic reagent capable of destroying RBC (red blood cells) and lysing WBC (white blood cells) and the established blood parameters are selected from the group consisting of WBC, PLT (platelets), POLY (polymorphonuclear cells) and MONO (mononuclear cells).

11. The method as in claim 6, wherein the step of picking up the ensemble light scattering pattern includes obtaining a measurement across a forward angle of between about 0° and about 10° relative to the blood specimen and the established blood parameters are selected from the group consisting of WBC (white blood cells), RBC (red blood cells), and PLT (platelets) concentration.

12. The method as in claim 6, wherein the of picking up the ensemble light scattering pattern includes picking up a multiple ring circularly symmetric scattering pattern wherein a diameter of a first ring corresponds to an average RBC (red blood cells) diameter.

13. The method as in claim 6, wherein the step of picking up the ensemble light scattering pattern includes taking intensity measurements at two angular intervals to generate first and second signals corresponding to the intensity of the ensemble scattered light within said angular intervals, and establishing the blood parameters of MCV, (mean cell volume) and MCHC (mean cell hemoglobin concentration) by comparing said first and second signals to corresponding signals generated from blood populations of known MCV and MCHC.

14. The method as in claim 6, further comprising the steps of interposing a mask on the ensemble light scattering pattern, measuring a masked value of intensity, comparing a value of unmasked intensity with the masked value of intensity and establishing the blood parameters selected from the group consisting of PLT (platelets)/RBC (red blood cells), GRAN (percentage of granulocytes)/WBC (white blood cells), GRAN/AGRAN (percentage of agranulocytes), MONO(percentage mononuclear cells)/POLY (percentage of polymorphonuclear cells), and POLY/WBC.

15. The method as in claim 14, wherein the mask is physical and is interposed precedent to the camera.

16. The method as in claim 14, comprising interposing a virtual mask.

17. The method as in claim 6, wherein the step of processing the digitized images comprises determining ensemble light scattering intensity as a function of time and the established blood parameter is ESR (enthrocyte sedimentation rate).

18. The method as in claim 6, wherein the step of processing the digitized images comprises determining fluctuations in ensemble light scattering intensity as a function of time and the established blood parameter is ESR (enthroyte Sedimentation rate).

* * * * *